US011925472B2

(12) United States Patent
Wang et al.

(10) Patent No.: US 11,925,472 B2
(45) Date of Patent: Mar. 12, 2024

(54) TRANSVAGINAL FAST-SCANNING OPTICAL-RESOLUTION PHOTOACOUSTIC ENDOSCOPY

(71) Applicants: Lihong Wang, Pasadena, CA (US); Konstantin Maslov, Pasadena, CA (US); Methodius Tuuli, Indianapolis, IN (US); Molly Stout, St. Louis, MO (US); George Macones, St. Louis, MO (US); Chiye Li, St. Louis, MO (US); Junhui Shi, Pasadena, CA (US); Yuan Qu, St. Louis, MO (US)

(72) Inventors: Lihong Wang, Pasadena, CA (US); Konstantin Maslov, Pasadena, CA (US); Methodius Tuuli, Indianapolis, IN (US); Molly Stout, St. Louis, MO (US); George Macones, St. Louis, MO (US); Chiye Li, St. Louis, MO (US); Junhui Shi, Pasadena, CA (US); Yuan Qu, St. Louis, MO (US)

(73) Assignees: Washington University, St. Louis, MO (US); California Institute of Technology, Pasadena, CA (US)

( * ) Notice: Subject to any disclaimer, the term of this patent is extended or adjusted under 35 U.S.C. 154(b) by 291 days.

(21) Appl. No.: 17/130,021

(22) Filed: Dec. 22, 2020

(65) Prior Publication Data
US 2021/0186411 A1    Jun. 24, 2021

Related U.S. Application Data

(60) Provisional application No. 62/952,940, filed on Dec. 23, 2019.

(51) Int. Cl.
*A61B 5/00* (2006.01)
*A61B 1/00* (2006.01)
(Continued)

(52) U.S. Cl.
CPC .......... *A61B 5/435* (2013.01); *A61B 1/00172* (2013.01); *A61B 1/07* (2013.01);
(Continued)

(58) Field of Classification Search
CPC ....... A61B 5/435; A61B 1/00172; A61B 1/07; A61B 1/303; A61B 5/0095;
(Continued)

(56) References Cited

U.S. PATENT DOCUMENTS

| 2011/0275890 A1* | 11/2011 | Wang | A61B 8/4461 600/104 |
| 2012/0310223 A1* | 12/2012 | Knox | A61F 9/00827 606/5 |
| 2015/0297092 A1* | 10/2015 | Irisawa | A61B 5/0095 600/407 |
| 2016/0058294 A1* | 3/2016 | Suzuki | A61B 5/7207 600/407 |

(Continued)

OTHER PUBLICATIONS

Xia J. et al. (2014) Photoacoustic tomography: principles and advances. Electromagn Waves (Camb). 2014; 147: 1-22.
(Continued)

*Primary Examiner* — Baisakhi Roy
*Assistant Examiner* — Kaitlyn E Sebastian

(57) ABSTRACT

The present disclosure describes a fast-scanning optical-resolution photoacoustic (fsOR-PAE) endoscope for imaging vasculature within tissues in vivo that includes an ultrasonic transducer and a scanning mirror within a lumen of an elongate casing. The scanning mirror is configured to direct the laser pulses from the pulsed laser source to a focal spot outside the casing in a scanning pattern via an imaging window formed in the casing. The scanning mirror is further configured to direct a plurality of photoacoustic signals from the focal spot to the ultrasonic transducer via the imaging window.

5 Claims, 10 Drawing Sheets
(10 of 10 Drawing Sheet(s) Filed in Color)

(51) Int. Cl.
  *A61B 1/07*   (2006.01)
  *A61B 1/303*  (2006.01)
  *A61B 5/02*   (2006.01)
  *G02B 26/08*  (2006.01)
  *G02B 26/10*  (2006.01)
  *G02F 1/17*   (2019.01)

(52) U.S. Cl.
  CPC ............ *A61B 1/303* (2013.01); *A61B 5/0095* (2013.01); *A61B 5/02007* (2013.01); *G02B 26/0833* (2013.01); *G02B 26/105* (2013.01); *G02F 1/17* (2013.01); *A61B 2562/028* (2013.01); *G02F 2203/48* (2013.01)

(58) Field of Classification Search
  CPC .......... A61B 5/02007; A61B 2562/028; G02B 26/0833; G02B 26/105; G02B 23/2469; G02F 1/17; G02F 2203/48
  See application file for complete search history.

(56) References Cited

U.S. PATENT DOCUMENTS

2016/0249812 A1* 9/2016 Wang ................. G01N 29/0681
                                                600/407
2018/0000351 A1* 1/2018 Zharov .............. G01N 15/1056

OTHER PUBLICATIONS

Strathman M. et al. (2015) MEMS scanning micromirror for optical coherence tomography. Biomed. Opt. Express, vol. 6, p. 211-224 (2015).

Li C. et al. (2014) Urogenital photoacoustic endoscope. Opt. Lett., vol. 39, p. 1473-1476.

Yao J. et al. (2012) Wide-field fast-scanning photoacoustic microscopy based on a water-immersible MEMS scanning mirror. J. Biomed. Opt., vol. 17, p. 080505.

* cited by examiner 0.5 mm 0.5 mm

TRANSVAGINAL FAST-SCANNING OPTICAL-RESOLUTION PHOTOACOUSTIC ENDOSCOPY

CROSS-REFERENCE TO RELATED APPLICATIONS

This application claims priority from U.S. Provisional Application Ser. No. 62/952,940 filed on Dec. 23, 2019, which is incorporated herein by reference in its entirety.

STATEMENT REGARDING FEDERALLY SPONSORED RESEARCH OR DEVELOPMENT

This invention was made with government support under EB016986 and CA186567 awarded by the National Institutes of Health. The government has certain rights in the invention.

FIELD OF THE DISCLOSURE

The present disclosure generally relates to methods of non-invasively imaging vascularization within human viscera in vivo. In particular, the present disclosure describes a transvaginal fast-scanning optical-resolution photoacoustic endoscope used to non-invasively image vascularization within human viscera in vivo.

BACKGROUND OF THE DISCLOSURE

Vasculatures enable nutrient transportation, waste disposal, and immune surveillance. Due to the diverse functions of blood vessels, abnormally morphological vascular changes are often associated with the development of various diseases, including tumor growth and metastasis, inflammatory disorders, and pulmonary hypertension, to name just a few. Many models linking vascular morphogenesis to the development of a particular disease have been developed for prognosis, diagnosis, or disease management. To apply these models in clinical assessment, however, a tissue biopsy from the lesion is typically needed. Because tissue biopsy is invasive and often not clinically feasible, technologies that provide in vivo noninvasive examination of vascular networks are clinically useful, but generally do not have enough resolution and specificity to resolve microcirculation vessels.

Optical-resolution photoacoustic microscopy using endogenous optical absorption contrast enables in vivo vascular imaging with a capillary-level spatial resolution, and it has emerged as a major tool for inspecting morphological changes in the vascular network. Photoacoustic endoscopy (PAE), by miniaturizing the tabletop setup of photoacoustic microscopy, can reach organs in body cavities and noninvasively acquire visceral vascular images. These endoscopic devices use rotary scanners, which enable a large angular field of view, up to ~310 deg, but also constrain the B-scan rate to ~10 Hz. As a result, motion artifacts due to the natural in vivo movement of tissue (breathing movement, peristalsis, etc.) often appear in the endoscopic images. Thus, the development of PAE systems with higher imaging speeds is a top priority to broaden its clinical application. Microelectromechanical system (MEMS) scanning mirrors have demonstrated their superior scanning speed, high accuracy, and simple system design in various biomedical imaging modalities. A water-immersible version with a small footprint has the potential to increase the imaging speed of PAE by an order of magnitude.

Other objects and features will be in part apparent and in part pointed out hereinafter.

DESCRIPTION OF THE DRAWINGS

The patent or application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

EC A32 denotes the ectocervix of the first patient after 32 weeks of gestation, EC A36 denotes the ectocervix of the first patient after 36 weeks of gestation, EC B36 denotes the ectocervix of the second patient after 36 weeks of gestation, EC S denotes the ectocervix specimen, SM S denotes the sublingual mucosa specimen, and UB S denotes the uterine body specimen ($*P<0.05$, $**P<0.01$).

Figure 7A:
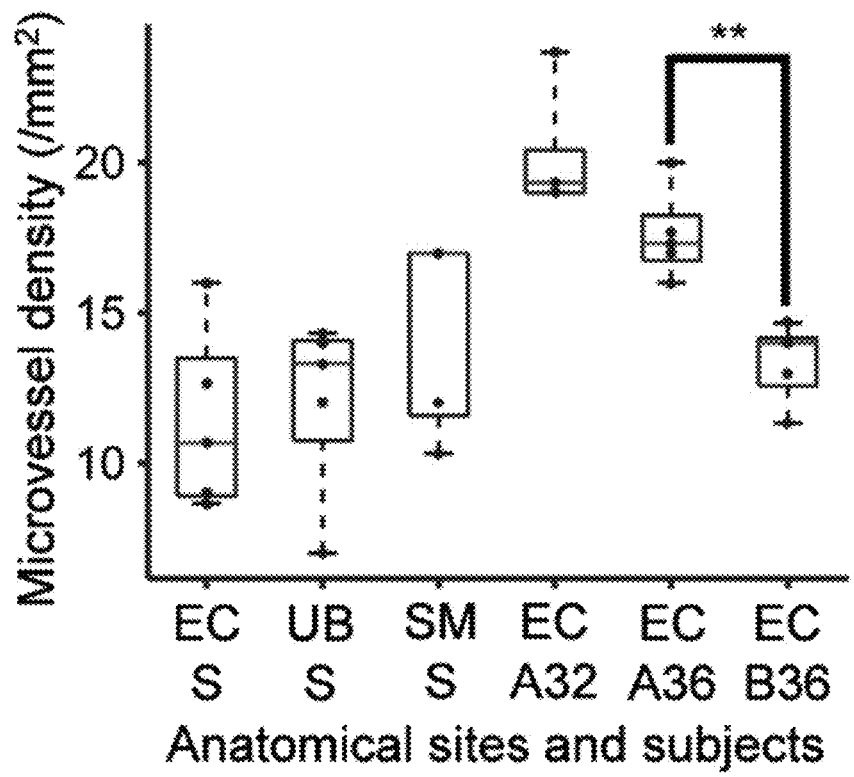
FIG. 7A is a box plot of microvessel density calculated from an analysis of fsOR-PAE images of microvessel density, in which five images were analyzed for each subject.
Figure 7B:
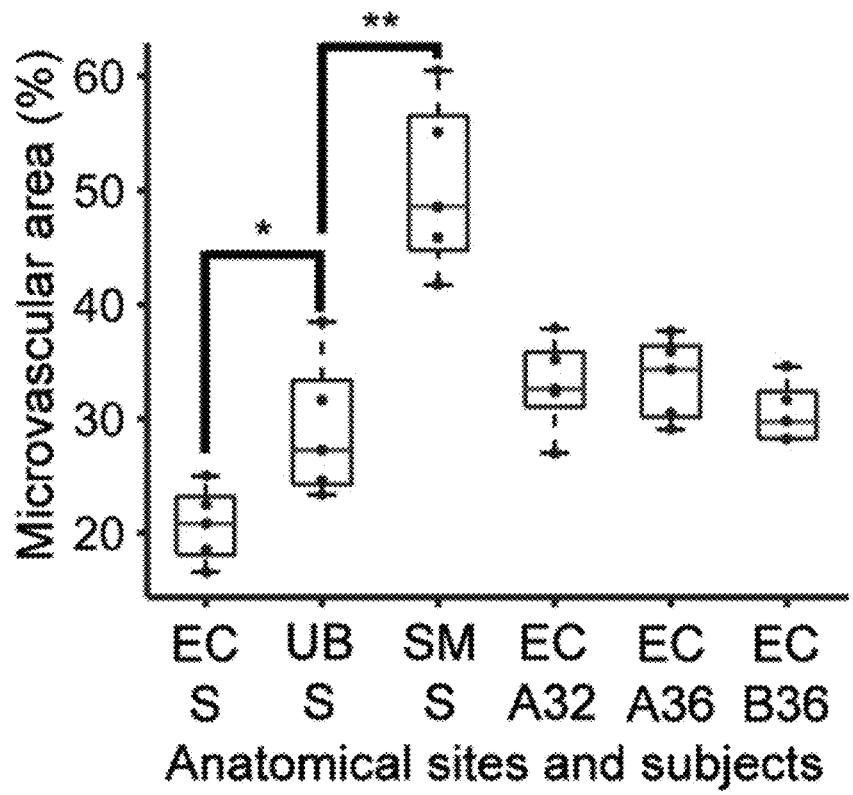

FIG. 7B is a box plot of total microvascular area calculated from analysis of fsOR-PAE images; five images were analyzed for each subject, annotated as described in FIG. 7A ($*P<0.05$, $**P<0.01$).

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION OF THE INVENTION

In various aspects, a transvaginal fast-scanning optical-resolution photoacoustic endoscope with a 250-Hz B-scan rate over a 3-mm scanning range is disclosed. Using this imaging modality, morphological differences of vasculatures among various human viscera may be assessed. Non-limiting examples of the various human viscera amenable to analysis using the disclosed endoscopic imaging system include human ectocervix, uterine body, and sublingual mucosa. The 3D images made possible by the disclosed endoscope enable the assessment of cross-sectional differences of cervical vasculatures in pregnant women. In addition, the non-invasive in vivo imaging of vasculatures obtained by the disclosed endoscope enable longitudinal assessments of vasculatures within human viscera including, but not limited to, monitoring longitudinal differences of cervical vasculatures in pregnant women as well as screening the visceral pathological changes associated with angiogenesis.

The disclosed endoscope and associated methods of use overcome at least one or more existing limitations of existing vasculature assessment methods. Some existing methods rely upon histological analysis of invasively-obtained biopsy samples which limit clinical use and/or preclude longitudinal monitoring of vasculature. Other existing photoacoustic endoscopy devices enable in vivo examination of the visceral tissue using endogenous contrast, but the speed of the scanning unit and the laser pulse repetition rate limits the B-scan rate of these existing devices to about 10 Hz, resulting in overly lengthy data acquisition times. Further, the resolution of existing endoscope devices are not sufficient for visualization of capillaries, limiting the clinically useful information obtained in vivo by existing endoscope devices.

In various aspects, a fast-scanning optical-resolution photoacoustic endoscope (fsOR-PAE) device is provided that includes a custom-designed MEMS scanning mirror configured to enable rapid spatial scanning during data acquisition. In one aspect, the B-scan rate of the fsOR-PAE reaches 250 Hz over a 3-mm range, representing a 10-fold improvement over existing photoacoustic endoscope devices. The enhanced imaging speed of the fsOR-PAE device enables the acquisition of visceral vascular images in humans in vivo, with a volumetric imaging speed of 0.75 Hz.

Figure 1A:
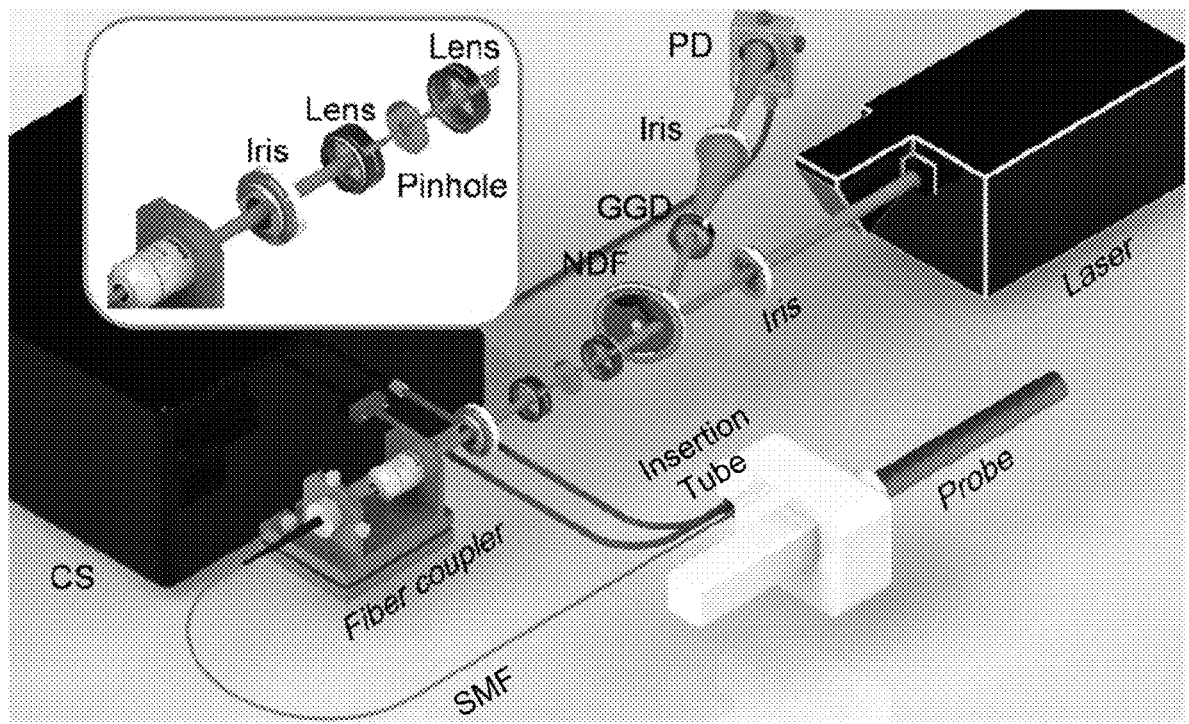
FIG. 1A is a schematic diagram of a fast-scanning optical-resolution photoacoustic endoscopy (fsOR-PAE) probe and its peripheral systems in accordance with one aspect of the disclosure. Illustrated elements include control system (CS), ground glass diffuser (GGD), variable neutral density filter (NDF), and photodetector (PD).

FIG. 1A is a schematic of the fsOR-PAE system in one aspect. The fsOR-PAE system is controlled by a custom-designed program written in LabVIEW (National Instruments). The system includes a fiber laser (V-Gen, VPFL-G-20) operating at 532-nm wavelength with a 500-kHz pulse repetition rate. Laser pulse energy is controlled by tuning a variable neutral density filter NDF so that the optical fluence on the tissue surface is below the American National Standards Institute safe exposure limit, but sufficient to induce the production of photoacoustic (PA) signals from the focal point illuminated by the laser pulse LP. In one aspect, the fiber laser is controlled to deliver laser pulses at an optical fluence of about 17 $mJ/cm^2$.

Referring again to FIG. 1A, the fsOR-PAE system further includes a photodetector PD (Thorlabs, PDA36A) coupled to the variable neutral density filter NDF and configured to detect the intensity of laser pulses LP reflected from the neutral density filter NDF. A voltage comparator (not illustrated) connected to the photodetector PD is configured to generate a trigger for each laser pulse LP in order to synchronize the operation of all elements of the fsOR-PAE system. The laser pulses LP are spatially filtered by a 50-μm diameter pinhole (Thorlabs, P50CH) before being coupled into a single-mode optical fiber SMF (Thorlabs, S405-XP). The single-mode optical fiber SMF guides the laser pulses LP into the fsOR-PAE probe using an insertion tube 20 cm in length and 20 mm in diameter (see FIG. 1B).

Figure 1B:
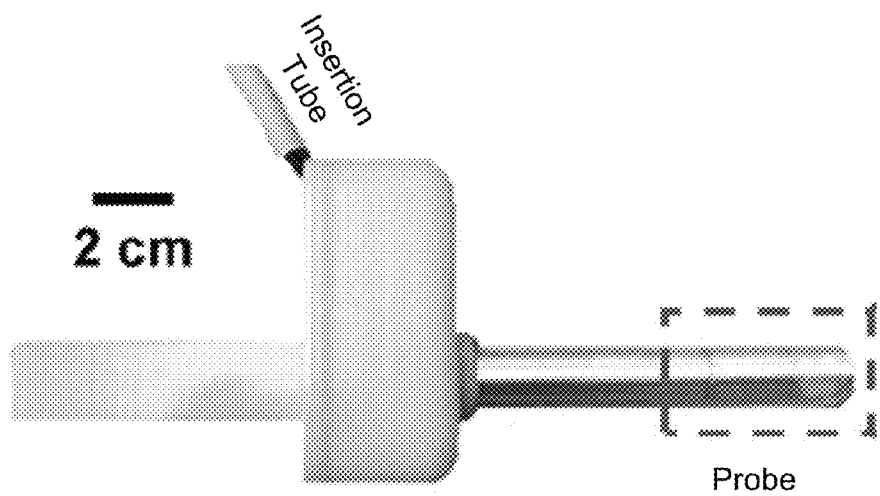
FIG. 1B is a photograph of the fsOR-PAE probe. A linear actuator positioned within the housing drives the azimuth scanning.
Figure 1C:
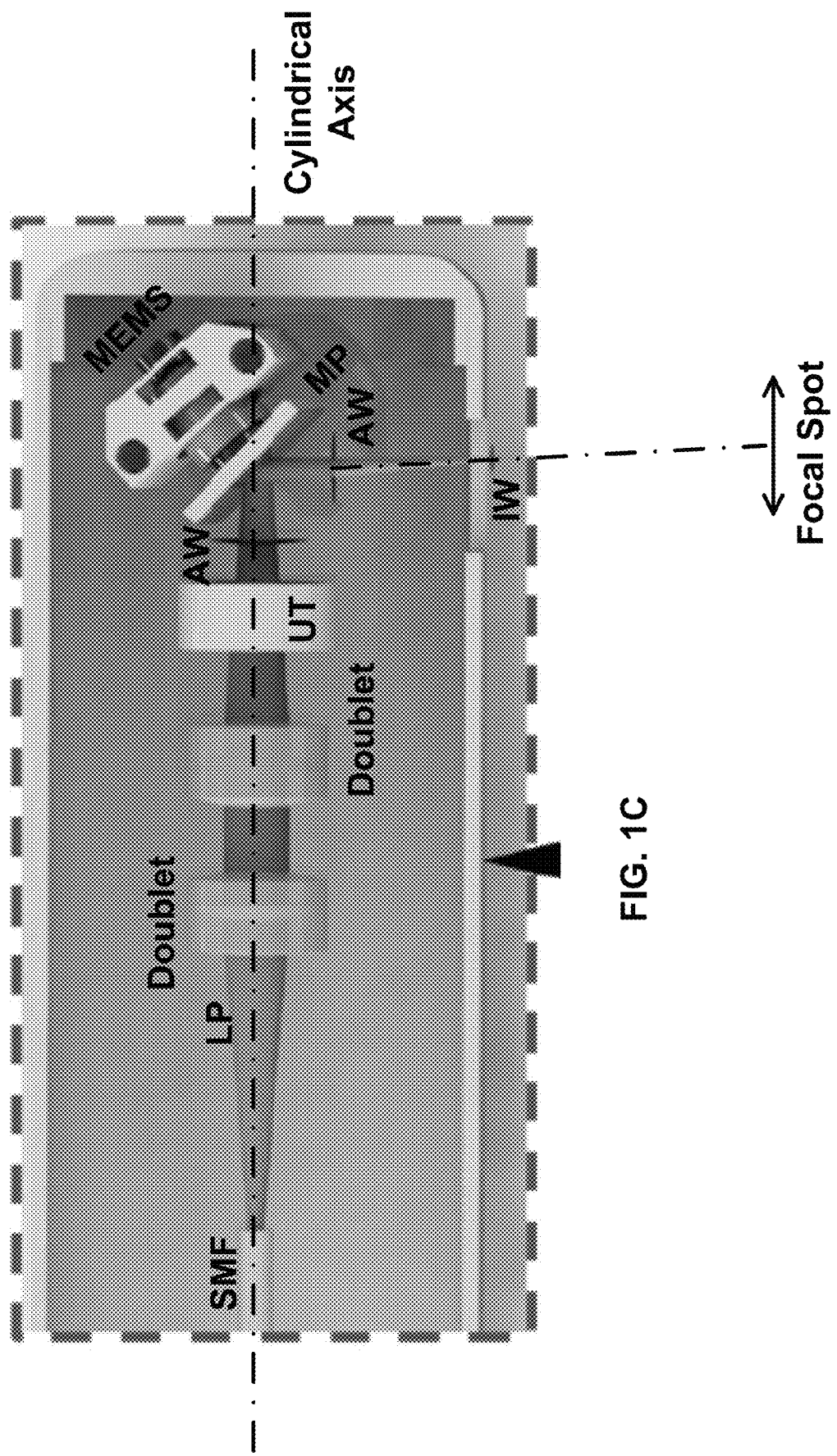
FIG. 1C is a cross-sectional schematic diagram illustrating acoustic-optical coaxial confocal alignment within the portion of the probe enclosed by the dashed rectangle of FIG. 1B, in which a MEMS actuator drives scanning parallel to the cylindrical axis. Illustrated elements include acoustic waves (AW), laser pulses (LP), microelectromechanical system scanning mirror (MEMS), single-mode fiber (SMF), imaging window (IW), and ultrasonic transducer (UT).

FIG. 1C is a cross-sectional view of the probe illustrated in FIG. 1B, illustrating an arrangement of probe elements within a lumen of a probes casing in one aspect. Within the probe casing, laser pulses LP from the single-mode fiber SMF are focused by a set of doublets DB (Thorlabs, AC064-015-A) and transmitted through the center of a custom-designed focused ultrasonic ring transducer UT (40-MHz central frequency). A MEMS scanning mirror directs the laser pulses LP through an imaging window IW to a focal spot within the tissues surrounding the probe. The imaging window IW is further configured to transmit acoustic waves AW (photoacoustic signals) produced at the focal spot in response to illumination by the laser pulses LP delivered by the probe. In one aspect, the MEMS scanning mirror is further configured to direct the acoustic waves AW transmitted though the imaging window IW to the ultrasonic transducer UT to be detected and used to reconstruct a photoacoustic image of the surrounding tissues. In various aspects, the laser pulses LP are directed from the probe to the focal spot along a optical path that is aligned with the corresponding acoustical path of the acoustic signals from the focal spot to the probe, achieving an acoustic-optical coaxial confocal alignment as illustrated in FIG. 1C.

In various aspects, the materials of the imaging window IW are selected to enhance optical and acoustic transmittances through the imaging window IW. In one aspect, a polymethylpentene membrane (CS Hyde, 33-3F-24) seals the imaging window, preventing leakage when the chamber of the probe is filled with distilled water for ultrasound coupling between the imaging window (IW) and the ultrasonic transducer (UT) within the probe.

Referring again to FIG. 1C, the MEMS scanning mirror includes a movable mirror plate MP configured to reflect laser pulses through the imaging window IW to the focal spot and to reflect acoustic waves AW received through the imaging window from the focal spot to the ultrasonic transducer UT. In one aspect, the mirror plate includes a polished silicon substrate, an aluminum reflective layer (200 nm), and a 20 nm-thick Sift protective overcoat. In one aspect, the mirror plate MP of the MEMS scanning mirror is supported by two hinges (0.75 mm in length, 0.5 mm in width, and 0.2 mm in thickness). In another aspect, the mirror plate MP has dimensions of 7 mm in length, 5 mm in width, and 1 mm in thickness.

Figure 2:
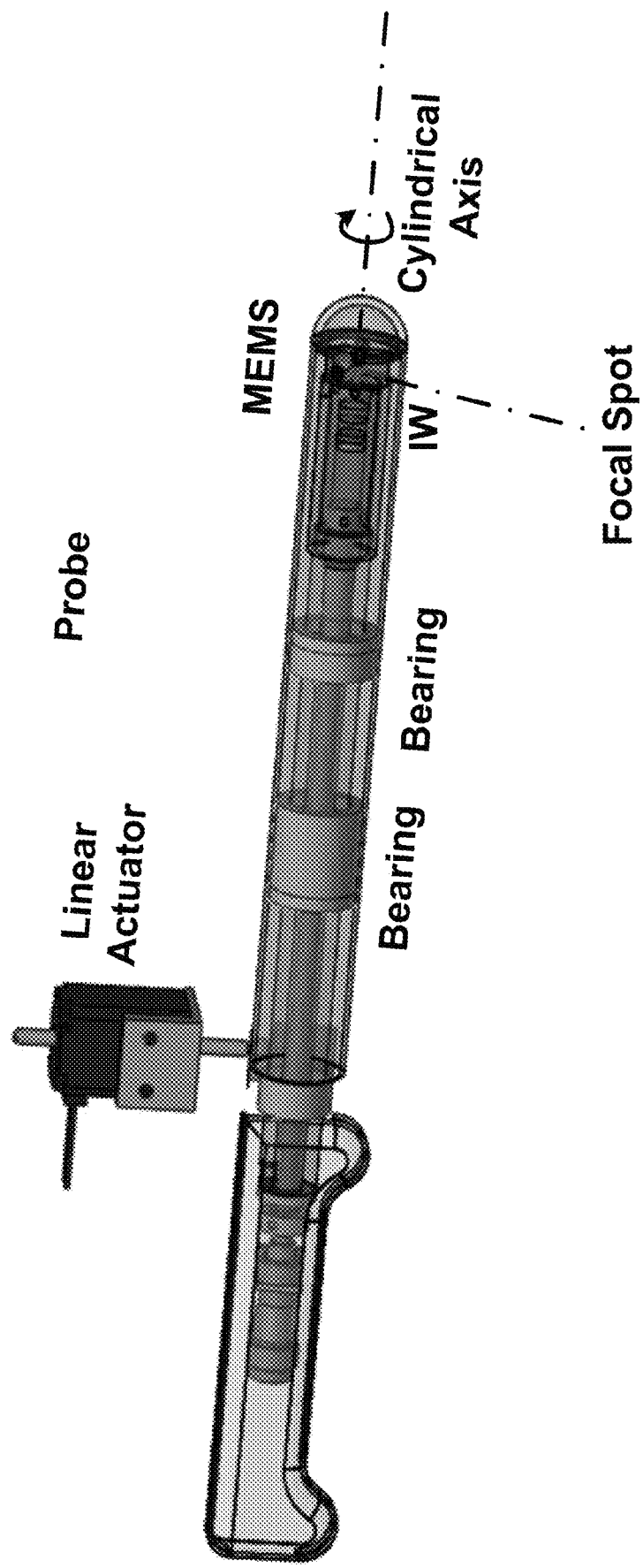
FIG. 2 is a schematic diagram illustrating a scanning mechanism of the fsOR-PAE probe of FIG. 1A.
Figure 3A:
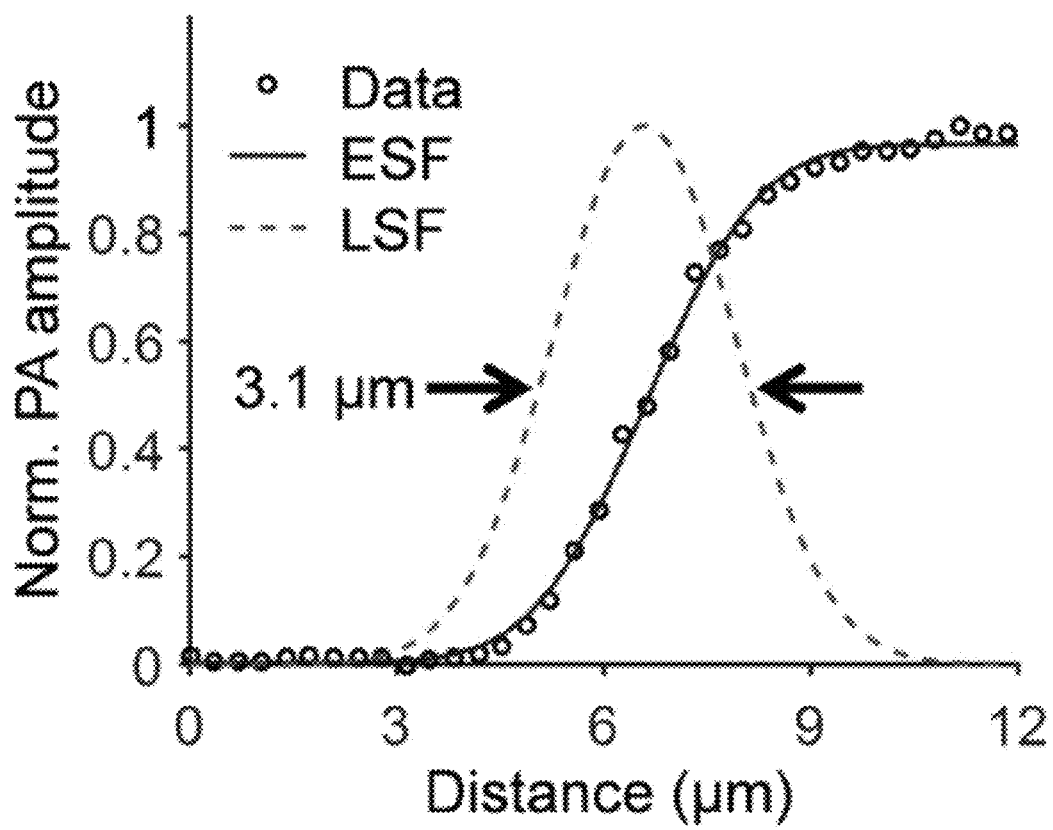
FIG. 3A is a graph summarizing the results of a lateral resolution test on a sharp edge conducted to characterize resolution of the fsOR-PAE probe. ESF denotes edge spread function and LSF denotes line spread function derived from ESF.
Figure 3B:
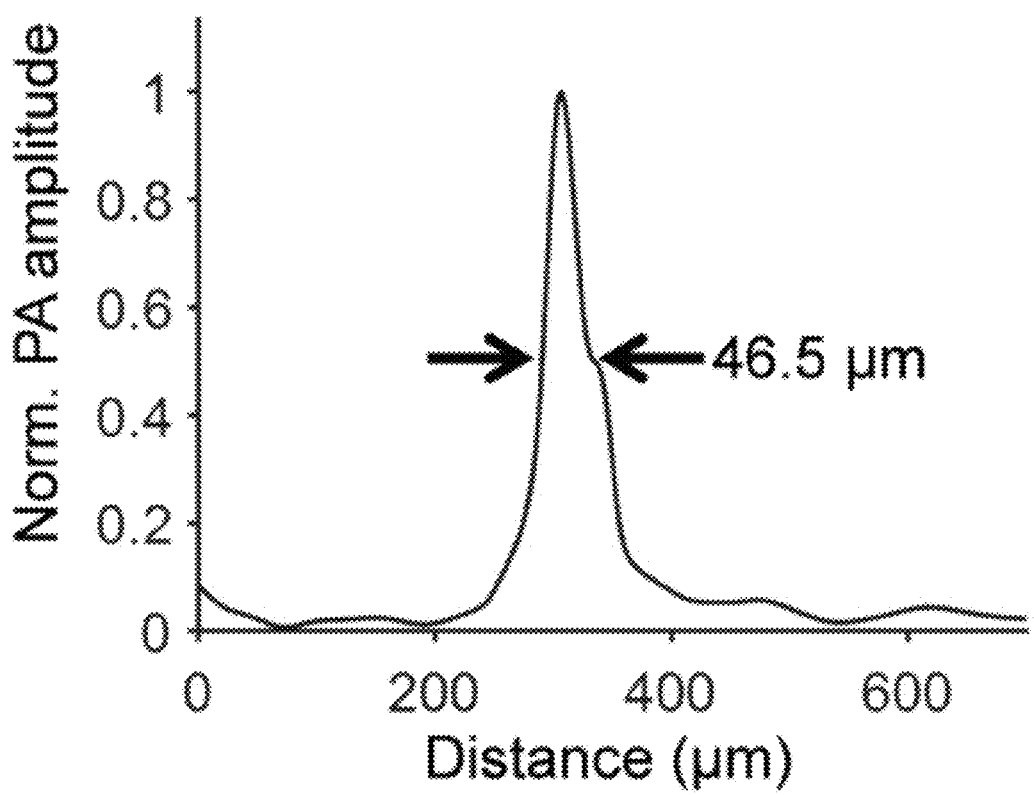
FIG. 3B is a graph summarizing the results of an axial resolution test on a tungsten wire conducted to characterize resolution of the fsOR-PAE probe.
Figure 3C:
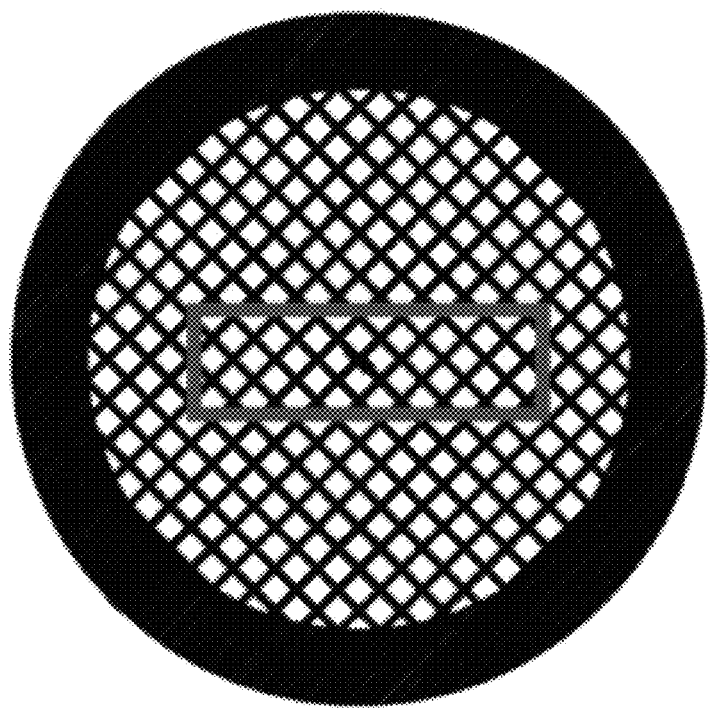
FIG. 3C is an image of a metal grid.

In various aspects, volumetric imaging of the tissues surrounding the probe is achieved by scanning the focal point in a scanning pattern including, but not limited to, scanning parallel to a cylindrical axis of the probe (see FIG. 3C), azimuthal scanning (see FIG. 2), and any combination thereof. In one aspect, the MEMS scanning mirror drives the focal spot scanning parallel to the cylindrical axis of the probe, as illustrated in FIG. 1C. During operation of the probe, fast scanning is enabled by rapid oscillation of the mirror plate MP actuated by a pair of permanent magnets fixed on the back of the mirror plate in one aspect. In this aspect, the mirror and attached magnets oscillate around the hinges in response to cyclic electromagnetic forces induced by sinusoidal current applied to a static inductor coil (inductance: 1 µH) of the MEMS device. In another aspect, azimuthal scanning, defined herein as rotation of the imaging window IW about the cylindrical axis of the probe, is driven by a linear actuator (Haydon Kerk, 21F4AC-2.5) as illustrated in FIG. 2. In one aspect, the linear actuator is positioned within the housing of the probe as illustrated in FIG. 1B. In another aspect, the linear actuator enables azimuthal scanning with a step size of about 3 µm.

In various aspects, the disclosed fsOR-PAE systems, devices, and methods enable high-resolution in vivo imaging of the vascular network in the human cervix with capillary-level spatial resolution that exceeds the resolution achievable using existing clinical methods. In some aspects, the size of the probe may be reduced further beyond the disclosed endoscope dimensions to reach smaller cavities in the human body. In some other aspects, the fsOR-PAE system may incorporate a dual-wavelength light source to enable the quantification of oxygen metabolism using oximetric methods. In additional other aspects, image analysis and classification models derived using artificial intelligence methods may be used to analyze images obtained using the fsOR-PAE system. Emerging AI-derived classification models may be used to extract latent information within these images which is beyond human recognition, but may be more valuable for diagnosis than the conventional histomorphological quantities extracted from the fsOR-PAE images as described herein.

As will be appreciated based upon the foregoing specification, the above-described aspects of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed aspects of the disclosure. The computer-readable media may be, for example, but is not limited to, a fixed (hard) drive, diskette, optical disk, magnetic tape, semiconductor memory such as read-only memory (ROM), and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one aspect, a computer program is provided, and the program is embodied on a computer readable medium. In one aspect, the system is executed on a single computer system, without requiring a connection to a sever computer. In a further aspect, the system is being run in a Windows® environment (Windows is a registered trademark of Microsoft Corporation, Redmond, Washington). In yet another aspect, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some aspects, the system includes multiple components distributed among a plurality of computing devices. One or more components may be in the form of computer-executable instructions embodied in a computer-readable medium. The systems and processes are not limited to the specific aspects described herein. In addition, components of each system and each process can be practiced independent and separate from other components and processes described herein. Each component and process can also be used in combination with other assembly packages and processes. The present aspects may enhance the functionality and functioning of computers and/or computer systems.

Embodiments of the disclosure may be described in the general context of computer-executable instructions, such as program modules, executed by one or more computers or other devices. The computer executable instructions may be organized into one or more computer executable components or modules. Generally, program modules include, but are not limited to, routines, programs, objects, components, and data structures that perform particular tasks or implement particular abstract data types. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer executable instructions or components having more or less functionality than illustrated and described herein. Aspects of the disclosure may also be practiced in distributed computing environments where tasks are performed by remote processing devices that are linked through a communications network. In a distributed computing environment, program modules may be located in both local and remote computer storage media including memory storage devices.

The computer systems, computing devices, and computer implemented methods discussed herein may include additional, less, or alternate actions and/or functionalities, including those discussed elsewhere herein. The computer systems may include or be implemented via computer executable instructions stored on non-transitory computer-readable media. The methods may be implemented via one or more local or remote processors, transceivers, servers, and/or sensors (such as processors, transceivers, servers, and/or sensors mounted on vehicle or mobile devices, or associated with smart infrastructure or remote servers), and/or via computer executable instructions stored on non-transitory computer-readable media or medium.

In some aspects, a computing device is configured to implement machine learning, such that the computing device "learns" to analyze, organize, and/or process data without being explicitly programmed. Machine learning may be implemented through machine learning (ML) methods and algorithms. In one aspect, a machine learning (ML) module is configured to implement ML methods and algorithms. In some aspects, ML methods and algorithms are applied to data inputs and generate machine learning (ML) outputs. Data inputs may include but are not limited to: images or frames of a video, object characteristics, and object categorizations. Data inputs may further include: sensor data, image data, video data, telematics data, authentication data, authorization data, security data, mobile device data, geolocation information, transaction data, personal identification data, financial data, usage data, weather pattern data, "big data" sets, and/or user preference data. ML outputs may include but are not limited to: a tracked shape output, categorization of an object, categorization of a type of motion, a diagnosis based on motion of an object, motion analysis of an object, and trained model parameters ML outputs may further include: speech recognition, image or video recognition, medical diagnoses, statistical or financial models, autonomous vehicle decision-making models, robotics behavior modeling, fraud detection analysis, user recommendations and personalization, game AI, skill acquisition, targeted marketing, big data visualization, weather forecasting, and/or information extracted about a computer device, a user, a home, a vehicle, or a party of a transaction. In some aspects, data inputs may include certain ML outputs.

In some aspects, at least one of a plurality of ML methods and algorithms may be applied, which may include but are not limited to: linear or logistic regression, instance-based algorithms, regularization algorithms, decision trees, Bayesian networks, cluster analysis, association rule learning, artificial neural networks, deep learning, dimensionality reduction, and support vector machines. In various aspects, the implemented ML methods and algorithms are directed toward at least one of a plurality of categorizations of machine learning, such as supervised learning, unsupervised learning, and reinforcement learning.

In one aspect, ML methods and algorithms are directed toward supervised learning, which involves identifying patterns in existing data to make predictions about subsequently received data. Specifically, ML methods and algorithms directed toward supervised learning are "trained" through training data, which includes example inputs and associated example outputs. Based on the training data, the ML methods and algorithms may generate a predictive function which maps outputs to inputs and utilize the predictive function to generate ML outputs based on data inputs. The example inputs and example outputs of the training data may include any of the data inputs or ML outputs described above. For example, a ML module may receive training data comprising customer identification and geographic information and an associated customer category, generate a model which maps customer categories to customer identification and geographic information, and generate a ML output comprising a customer category for subsequently received data inputs including customer identification and geographic information.

In another aspect, ML methods and algorithms are directed toward unsupervised learning, which involves finding meaningful relationships in unorganized data. Unlike supervised learning, unsupervised learning does not involve user-initiated training based on example inputs with associated outputs. Rather, in unsupervised learning, unlabeled data, which may be any combination of data inputs and/or ML outputs as described above, is organized according to an algorithm-determined relationship. In one aspect, a ML module receives unlabeled data and module employs an unsupervised learning method such as "clustering" to identify patterns and organize the unlabeled data into meaningful groups. The newly organized data may be used, for example, to extract further information.

In yet another aspect, ML methods and algorithms are directed toward reinforcement learning, which involves optimizing outputs based on feedback from a reward signal. Specifically ML methods and algorithms directed toward reinforcement learning may receive a user-defined reward signal definition, receive a data input, utilize a decision-making model to generate a ML output based on the data input, receive a reward signal based on the reward signal definition and the ML output, and alter the decision-making model so as to receive a stronger reward signal for subsequently generated ML outputs. The reward signal definition may be based on any of the data inputs or ML outputs described above. In one aspect, a ML module implements reinforcement learning in a user recommendation application. The ML module may utilize a decision-making model to generate a ranked list of options and may further receive selection data based on a user selection of one of the ranked options. A reward signal may be generated based on comparing the selection data to the ranking of the selected option. The ML module may update the decision-making model such that subsequently generated rankings more accurately predict a user selection.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following examples illustrate various aspects of the disclosure.

Example 1: Lateral and Axial Resolution of fsOR-PAE System

To test the performance of the fsOR-PAE system, tissue-mimicking phantoms were imaged to assess lateral and axial resolution. The lateral resolution of fsOR-PAE was quantified by imaging the edge of a sharp blade. As summarized in FIG. 3A, an edge spread function (ESF) was obtained from the imaging data. A line spread function (LSF) was computed and found to have a full width at half maximum of 3.1 μm, which represents the lateral resolution.

To estimate the axial resolution of the fsOR-PAE system, a tungsten wire (diameter: 14 μm) was imaged. As summarized in FIG. 3B, an edge spread function (ESF) was obtained from the imaging data. Based on the ESF shown in FIG. 3B, axial resolution was estimated to be 46.5 μm.

Figure 3D:
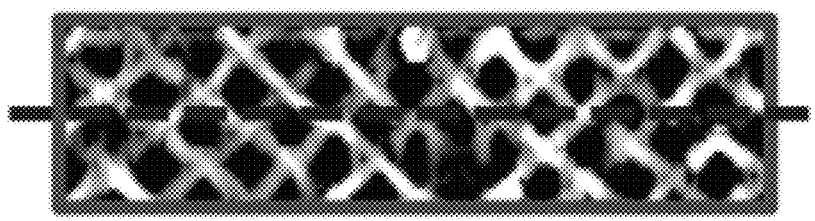
FIG. 3D is a maximum amplitude projection image computed from the region enclosed by the red rectangle in FIG. 3C.
Figure 3E:
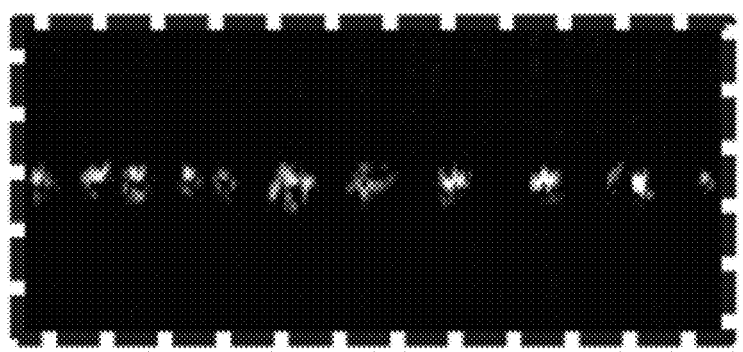
FIG. 3E is a B-scan image in the plane highlighted by the blue dashed line in FIG. 3D.

To further assess image resolution of images obtained using the fsOR-PAE system, a metal grid with a 127-μm pitch and a 37-μm bar width (see FIG. 3C) was imaged. FIG. 3D is a reconstructed PA image of a region of the metal grid within the red rectangle region of FIG. 3C. The average signal-to-noise ratio (SNR) of the imaging data was 33.2 dB. FIG. 3E is a B-scan image obtained from the plane highlighted by the dashed line in FIG. 3D. Because the angular scanning of fsOR-PAE maps the detected photoacoustic signals in polar coordinates, the imaging data were transformed from polar coordinates to Cartesian coordinates for image reconstruction. These results suggested that the fsOR-PAE system is capable of imaging structures on the micrometer scale.

Example 2: Ex Vivo Imaging of Human Tissues Using fsOR-PAE System

Figure 4C:
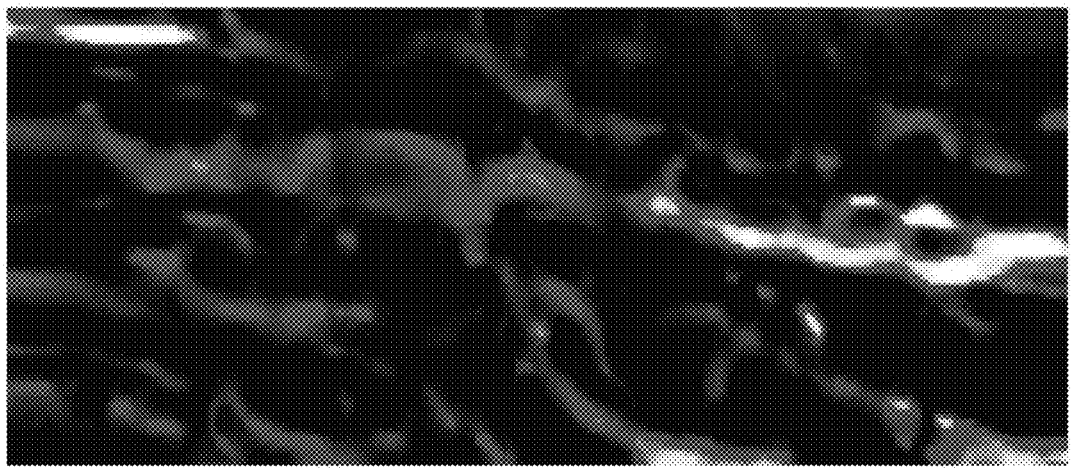
FIG. 4C is an ex vivo fsOR-PAE image of a sublingual mucosa.
Figure 4B:
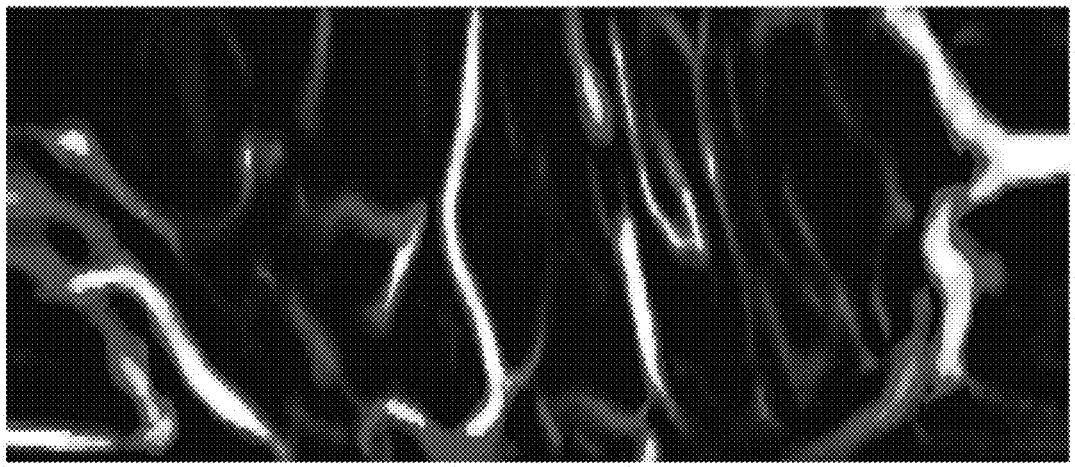
FIG. 4B is an ex vivo fsOR-PAE image of a serosal layer of a uterine body.
Figure 4A:
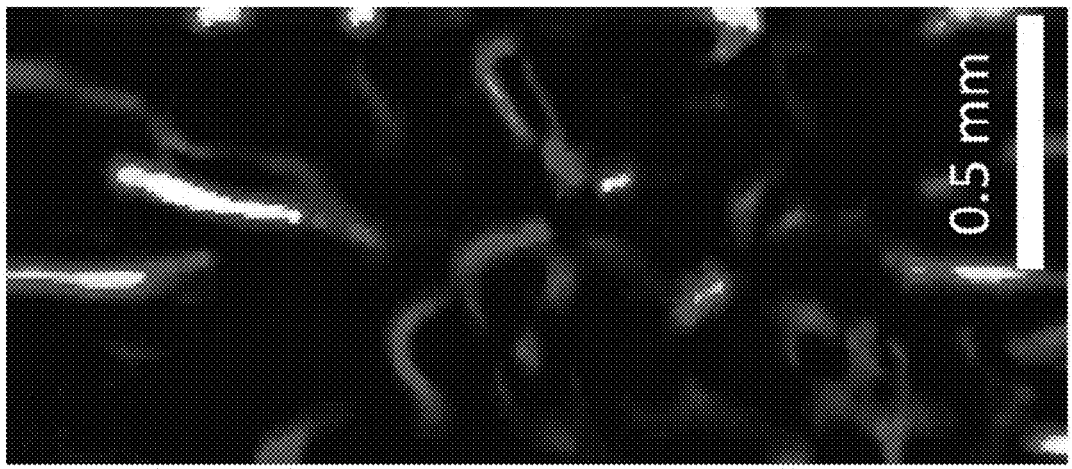
FIG. 4A is an ex vivo fsOR-PAE image of a human ectocervix.
Figure 5:
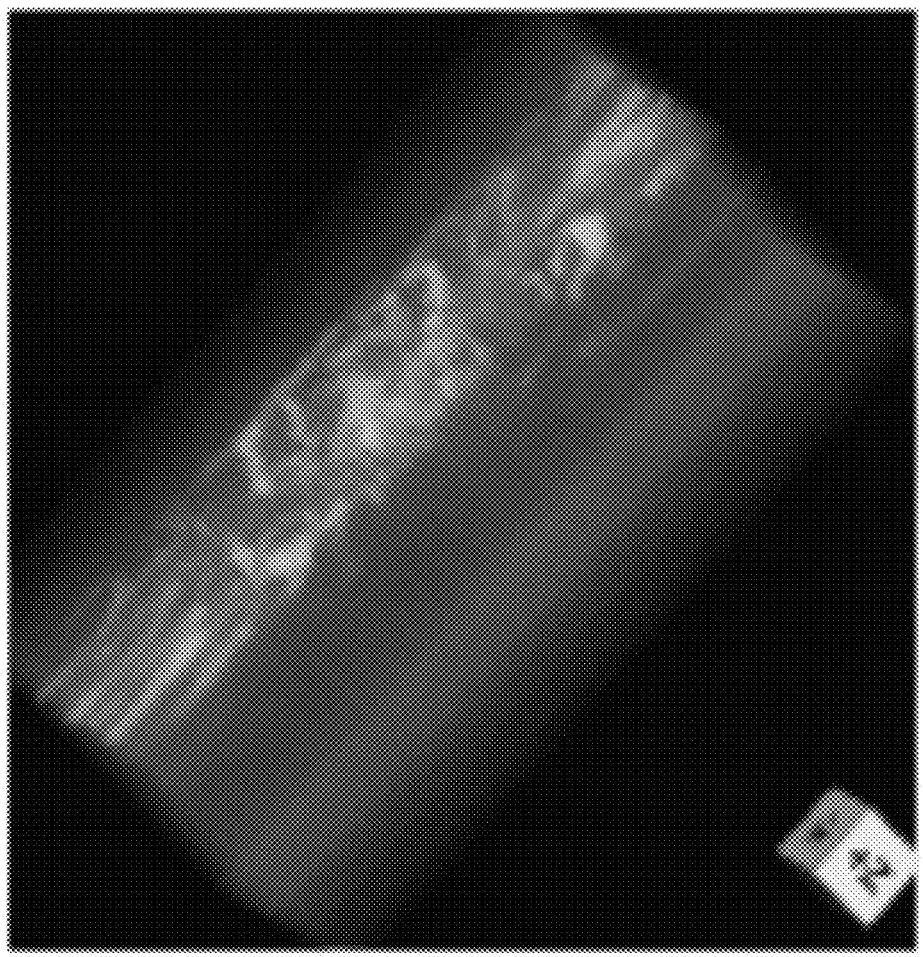
FIG. 5 is a volume-rendered image reconstructed from fsOR-PAE imaging data.

Various human tissues were imaged to further demonstrate the imaging capability of fsOR-PAE in a biological context. In one experiment, a uterus obtained from hysterectomy was imaged ex vivo using the fsOR-PAE system. FIG. 4A and FIG. 4B are reconstructed images showing the vascular networks in the ectocervix and the serosal layers of the uterine body, respectively. FIG. 5 is a volume-rendered image of the uterus shown in FIG. 4A and FIG. 4B.

Viewed as a projection on the coronal plane, the blood vessels in the ectocervix (FIG. 4A) were more likely to have a small aspect ratio and to be oriented toward the sagittal plane. In addition, the morphology of the vascular network clearly varied from one tissue to another. For example, blood vessels longer than 2 mm were absent in the ectocervix (FIG. 4A), but these long blood vessels were easily found in an image of human sublingual mucosa shown in FIG. 4C, which was also obtained using the fsOR-PAE system.

Figure 4D:
FIG. 4D is a standard hematoxylin and eosin histology image of the ectocervix shown imaged in FIG. 4A obtained after completion of fsOR-PAE imaging, showing no tissue damage.

To demonstrate the safety of the fsOR-PAE system, the uterine tissues imaged as shown in FIGS. 4A and 4B were subjected to histological analysis. The uterine tissue was stained using standard hematoxylin and eosin stains and examined using microscope images, as shown in FIG. 4D. The histology images showed no evidence of tissue damage, necrosis, or heat injury resulting from imaging using the fsOR-PAE system.

Example 3: In Vivo Imaging of Human Tissues Using fsOR-PAE System

To demonstrate the in vivo imaging capabilities of the fsOR-PAE system, in vivo images were obtained from human subjects. Previous studies found that cervical remodeling during pregnancy was associated with increased vascularity. The fsOR-PAE system was used to monitor vascular remodeling during pregnancy in vivo.

Figure 6C:
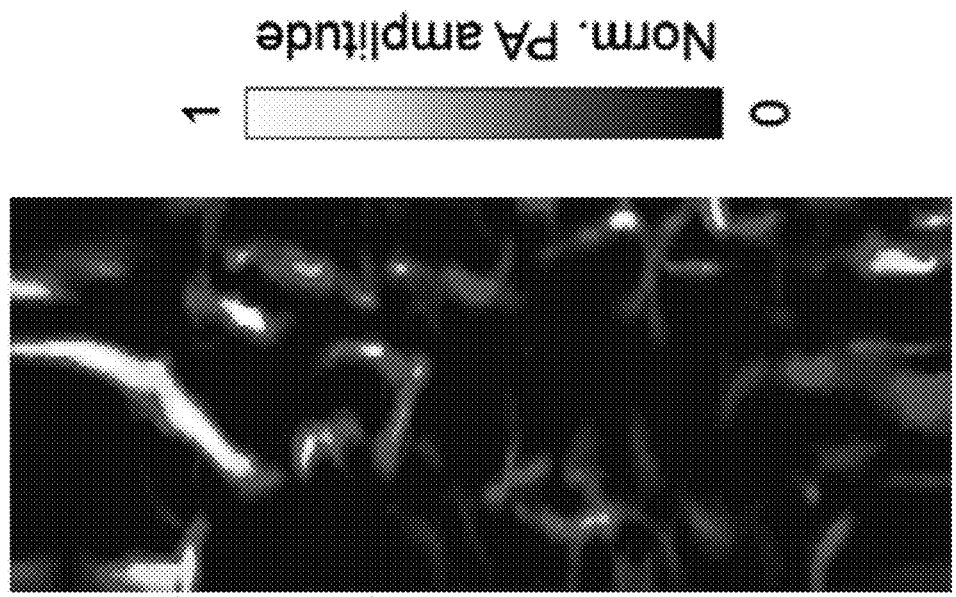
FIG. 6C is an in vivo fsOR-PAE image acquired from a second subject after 36 weeks of gestation.
Figure 6B:
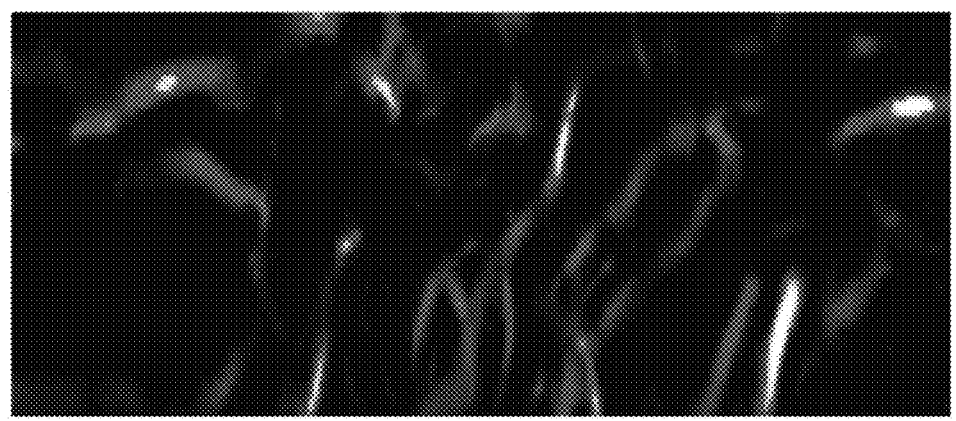
FIG. 6B is an in vivo fsOR-PAE image acquired from the first subject after 36 weeks of gestation.
Figure 6A:
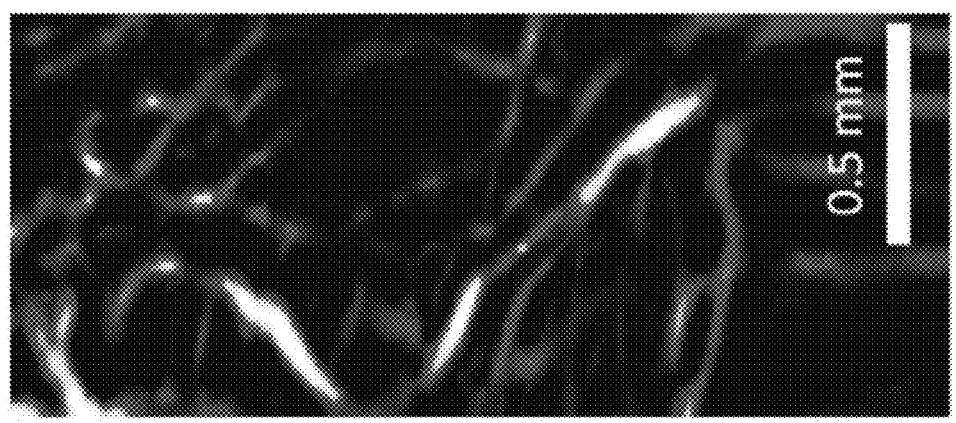
FIG. 6A is an in vivo fsOR-PAE image acquired from a first subject after 32 weeks of gestation.

Two pregnant women were selected as subjects and their anterior ectocervix surfaces were imaged using the fsOR-PAE system. The first subject was 30 years old, had two prior deliveries, and had an operative vaginal delivery for nonreassuring fetal status at 39 weeks of gestation. The second subject was 24 years old, had one prior delivery, and labored at 38 weeks of gestation. The first subject was imaged at 32 weeks and 36 weeks of gestation. The reconstructed images of the anterior surface of the ectocervix obtained at 32 and 36 weeks of gestation are shown in FIG. 6A and FIG. 6B, respectively. In the first subject, no perceptible changes in vascular aspect ratio or blood vessel orientation were observed over this time frame.

The second subject was imaged to perform a between-subject comparison. A reconstructed image of the anterior surface of the ectocervix obtained at 36 weeks of gestation is shown in FIG. 6C. Comparing FIG. 6B to FIG. 6C, the blood vessels in the ectocervix of subject 2 (FIG. 6C) had a smaller aspect ratio than in subject 1 (FIG. 6B) at the same gestational age (36 weeks).

Example 4: Analysis of Images Obtained Using fsOR-PAE System

To demonstrate the identification of physiological features by analysis of fsOR-PAE images, the following experiments were conducted. fsOR-PAE images of the specimens of Ex. 2 and of the subjects of Ex. 3 were analyzed to identify two vascular parameters potentially indicative of cervical remodeling: (1) the microvessel density (the number of vessels per unit area) and (2) total microvascular area (the percentage of area occupied by blood vessels). Each parameter was calculated from five images measured from different areas of the samples/subjects. In the analysis, the blood vessels were segmented in three-dimensional (3-D) space, using a threshold set at three times the noise level; noise level was estimated as the standard deviation of the background signal outside the imaged region. The segmented outcomes were visually inspected and corrected if necessary. FIG. 7A and FIG. 7B summarize microvessel densities and microvascular areas obtained by analysis of the fsOR-PAE images as described above, respectively. As illustrated in FIG. 7A, no differences in microvessel density were observed between the different tissue types of the ex vivo samples (EC S, UB S, and SM S), but significant differences were observed between different in vivo images (EC A32, EC A36, and EC B36) demonstrating that microvessel density was potentially useful for identifying the progress of cervical remodeling. As illustrated in FIG. 7B, no differences in microvessel density were observed between different in vivo images, but significant differences were observed between the different tissue types of the ex vivo samples, demonstrating that total microvascular area was potentially useful for classifying the type of tissue.

What is claimed is:

1. A method of imaging a microvasculature within a tissue using a fast-scanning optical-resolution photoacoustic (fsOR-PAE) system, the method comprising:
   providing an fsOR-PAE endoscope comprising a scanning mirror and an ultrasonic transducer housed within an elongate housing, a set of doublets positioned between a pulsed laser source and the scanning mirror, and the pulsed laser source, the pulsed laser source and the ultrasonic transducer coupled to the scanning mirror;
   positioning the elongate housing within the tissue;
   producing a plurality of laser pulses using the pulsed laser;
   focusing the plurality of laser pulses using the set of doublets pulses;
   directing the plurality of laser pulses through an imaging window formed within the housing to a plurality of focal spots within the tissue in a scanning pattern using the scanning mirror, wherein directing the plurality of laser pulses in a scanning pattern comprises scanning in a sweep parallel to cylindrical axis and a B-scan rate of 250 Hz over a 3 mm range;
   receiving and directing a plurality of photoacoustic signals produced at the plurality of focal spots to the ultrasonic transducer via the imaging window;
   detecting the plurality of photoacoustic signals using the ultrasonic transducer; and
   transforming the plurality of detected photoacoustic signals into an image of the microvasculature, wherein the image comprises a lateral resolution of less than 5 µm.

2. The method of claim 1, wherein the scanning pattern further comprises scanning the imaging window in an azimuthal scanning pattern.

3. The method of claim 1, wherein the plurality of laser pulses are delivered at a wavelength of about 532 nm, at a pulse repetition rate of about 500 kHz, and at an optical fluence of less than about 17 mJ/cm$^2$.

4. The method of claim 1, wherein transforming the plurality of detected photoacoustic signals further comprises reconstructing the plurality of detected photoacoustic signals into the image using a reconstruction method.

5. The method of claim 4, wherein the reconstruction method comprises a back-projection reconstruction method.

* * * * *